(12) United States Patent
Harms et al.

(10) Patent No.: US 6,316,252 B1
(45) Date of Patent: Nov. 13, 2001

(54) BIOTHERAPEUTIC DELIVERY SYSTEM

(75) Inventors: Jerome S. Harms, Madison; Gary A. Splitter, Brooklyn, both of WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/213,343

(22) Filed: Dec. 17, 1998

(51) Int. Cl.$^7$ .............................. C12N 15/38; C07H 21/04
(52) U.S. Cl. ................ 435/320.1; 435/69.7; 530/350; 530/826; 536/23.4; 536/27.72
(58) Field of Search ..................... 435/69.7, 320.1; 530/350, 826; 536/23.4, 23.72

(56) References Cited

U.S. PATENT DOCUMENTS

| | | | |
|---|---|---|---|
| 5,491,084 | * | 2/1996 | Chalfie et al. ................ 435/189 |
| 5,776,427 | * | 7/1998 | Thorpe et al. ................ 424/1.49 |
| 6,017,735 | * | 1/2000 | O'Hare et al. ................ 435/69.7 |
| 6,184,038 | * | 2/2001 | O'Hare et al. ................ 435/455 |

FOREIGN PATENT DOCUMENTS

WO 97/05265 * 2/1997 (WO) .

OTHER PUBLICATIONS

Harms et al., Distinctions between Bovine Herpesvirus 1 and Herpes Simplex Virus Type 1 VP22 Tegument Protein Subcellular Associations. Journal of Virology 74(7):3301–3312, 2000.*

G. Elliott et al., The herpes simplex virus type 1 tegument protein VP22 is encoded by gene UL49, 73 J. Virol. 723–726 (1992).

G. Elliott et al., Intercellular Trafficking and Protein Delivery by a Herpesvirus Structural Protein, 88 Cell 223–233 (1997).

A. Phelan et al., Intercellular delivery of functional p53 by the herpesvirus protein VP22, 16, Nature Biotech. (May, 1998) (Applicant reserves the right to determine whether this is prior art).

X. Liang et al., excerpt from 69 J. Virol. 3863 (1995) in NCBI nucleotide listing—Bovine herpesvirus 1 virion tegument protein gene, (1996).

X. Liang, et al., Characterization of Bovine Herpesvirus 1 UL49 Homolog Gene and Product: Bovine Herpesvirus 1 UL49 Homolog Is Dispensable for Virus Growth, 69 J. Virol. 3863–3867 (1995).

X. Liang et al., Study of immunogenicity and virulence of bovine herpesvirus 1 mutants deficient in the UL49 homolog, UL49.5 homolog and dUTPase genes in cattle, 15 Vaccine 1057–1064 (1997).

B. Lamy et al., Isolation and nucleotide sequence of the *Aspergillus restrictus* gene coding for the ribonucleolytic toxin restrictocin and its expression in *Aspergillus nidulans* . . . , 19 Nuc. Acids Res. 1001–1006 (1991).

B. Lamy et al., excerpt from Exhibit 4—A. restrictus restrictocin gene (1991).

D. Prasher et al., excerpt from 111 Gene 229–233 (1992) in NCBI nucleotide listing—*Aequorea victoria* green–fluorescent protein mRNA, complete cds. (1992).

* cited by examiner

Primary Examiner—Donna C. Wortman

(57) ABSTRACT

Disclosed herein are fusion proteins, nucleotide sequences for creating them, and vectors containing the nucleotide sequences. The fusion proteins have a bovine herpesvirus protein linked to a biotherapeutic protein or reporter protein. They rapidly spread biotherapeutic or reporter protein throughout mammalian cells.

**4 Cla

BIOTHERAPEUTIC DELIVERY SYSTEM

STATEMENT REGARDING FEDERALLY SPONSORED RESEARCH

Figure 1:
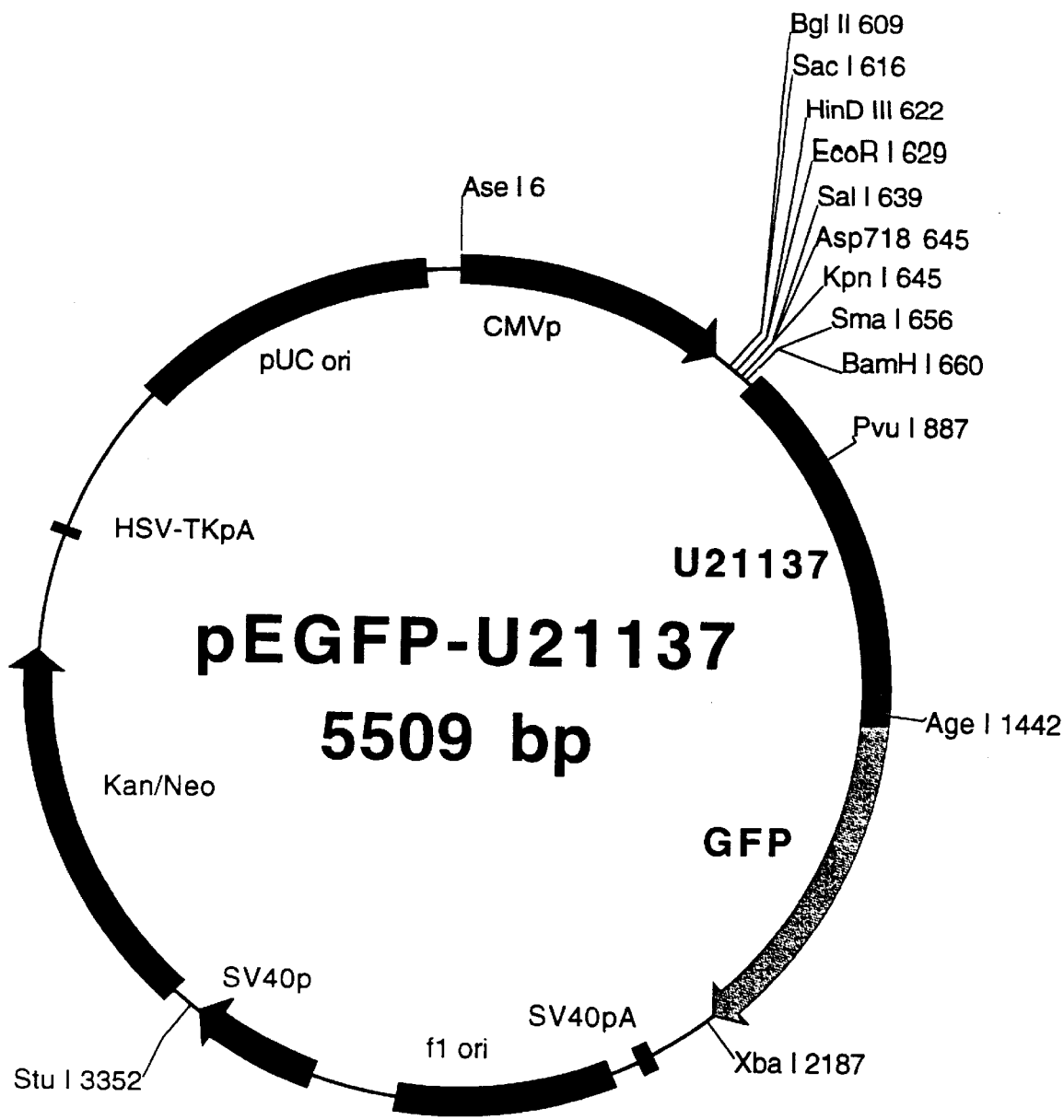

This invention was made with United States government support awarded by the following agency: USDA Grant No: 96-35204-3670. The United States has certain rights in this invention.

CROSS REFERENCES TO RELATED APPLICATIONS

Not applicable.

BACKGROUND OF THE INVENTION

The present invention relates to a transport peptide for delivering therapeutic and reporter proteins into cells, and vectors capable of expressing such proteins. More specifically it relates to the use of a bovine herpesvirus protein as part of a fusion protein that can be used for such purposes.

An important challenge facing the biomedical field is the need to provide effective methods to introduce therapeutic and reporter proteins into cells. While various existing approaches are adequate in some situations, they are usually deficient in others.

In G. Elliott et al., 73 J. Gen. Virol. 723–726 (1992); G. Elliott et al., 88 Cell 223–233 (1997); and A. Phelan et al., 16 Nat. Biotech. 440–443 (May 1998) the authors describe a human herpesvirus protein "HSV-VP22". They suggest that it may assist the delivery of proteins that are fused to it to surrounding cells. The disclosure of these publications and of all other publications referred to herein are incorporated by reference as if fully set forth herein.

However, there are safety concerns involved in using proteins from human herpesvirus in vivo in a human, and the efficiency of such a system appears to be undesirably low.

Moreover, the HSV-VP22 protein is a relatively large protein. Thus, due to its size, it is projected to be more likely to interfere with the activity of certain linked effectors, and/or may induce an antibody response.

In X. Liang et al., 69 J. Virol. 3863–3867 (1995) and X. Liang et al., 15 Vaccine 1057–1064 (1997) a bovine herpesvirus gene was described. In X. Liang et al., NCBI Entrez, (Accession U21137) (1996) the nucleotide sequence of this bovine gene (SEQ ID NO: 1) and its protein product (SEQ ID NO: 2) were provided. The gene was being studied in connection with vaccine research.

HSV VP22 is a 38 kD protein of 302 amino acids (906 bp of DNA) while the aforesaid bovine protein is a 32 kD protein of 259 amino acids (777 bp of DNA). Further, utilizing a computer program we determined that there was only about 28.7% amino acid identity between the two proteins.

A need therefore exists for an improved delivery system for delivering biotherapeutic proteins of interest to mammalian cells.

BRIEF SUMMARY OF THE INVENTION

In one aspect the invention provides a peptide which is SEQ ID NO: 2 bovine herpesvirus protein linked to a non-bovine protein selected from the group consisting of therapeutic proteins and reporter proteins. Almost any proteinaceous material that can serve a human or animal therapeutic purpose (e.g. drugs such as enzymes, vaccines, transcription factors, and viral inhibitors) can be linked to the bovine protein and then delivered using the fusion protein. It does not appear to be critical which of the two proteins are at the N-terminus.

As an example we selected a known anti-cancer toxin (restrictocin) (see generally B. Lamy et al., 19 Nuc. Acid. Res. 1001–1006 (1991) and B. Lamy et al., NCBI Entrez, (Accession X56176) (1991)(DNA and amino acid sequence) and SEQ ID NO: 3 (which also provides the amino acid sequence of this toxin protein)).

Alternatively, the SEQ ID NO: 2 protein can be linked to an innocuous reporter protein, such as the Aequorea victoria green fluorescent protein described in D. Prasher et al., NCBI Entrez (Accession M62654) (1992) (DNA and amino acid sequence). See also SEQ ID NO: 4 which also provides the amino acid sequence of that protein. Various other reporter proteins (e.g. radioactive; color indicating; and bioluminescent) can be used such as β-galactosidase or luciferase.

In another aspect, the invention provides a nucleotide sequence coding for SEQ ID NO: 2 bovine herpesvirus protein linked to a non-bovine protein selected from the group consisting of therapeutic proteins and reporter proteins. A preferred coding sequence for the SEQ ID NO: 2 protein is nucleotides 390 through 1161 of SEQ ID NO: 1, with the following insertions made at the end of the bovine gene starting at nucleotide 1162: acc ggt cgc, followed by an insertion of cac c, followed by the atg of the fusion protein.

In another aspect, the invention provides a nucleotide vector having a vector backbone and a nucleotide sequence coding for SEQ ID NO: 2 bovine herpesvirus protein linked to a non-bovine protein selected from the group consisting of therapeutic proteins and reporter proteins. The vector may be any nucleotide vector that a cell will accept and permit to express within the cell (e.g. plasmid vectors, viral vectors). A preferred vector is a mammalian expression plasmid having a promoter and marker.

The invention is primarily intended for delivering therapeutic and/or reporter proteins to mammalian cells, either in vitro or in vivo. It appears to be especially well suited to deliver such proteins to ruminant and primate (e.g. human) cells. It therefore has in vivo and in vitro pharmaceutical, veterinary and research applications.

The objects of the present invention therefore include providing:

(a) fusion proteins of the above kind that are suitable to deliver biotherapeutic proteins and/or reporter genes to cells of interest;

(b) nucleotide sequences of the above kind that can express such proteins in cells; and (c) recombinant nucleotide vectors capable of delivering such nucleotide sequences to cells. These and still other objects and advantages of the present invention will be apparent from the description which follows. The following description is merely of the preferred embodiments. Thus, the claims should be looked to in order to understand the full scope of the invention.

BRIEF DESCRIPTION OF THE DRAWING

FIG. 1 is a schematic sketch of plasmid pEGFP-U21137, which is a preferred vector of the present invention.

DETAILED DESCRIPTION

General Overview

The SEQ ID NO: 2 protein is a protein that has efficient intercellular transport. When the protein is introduced via DNA constructs that express it, following expression in a sub-population, the expressed protein rapidly spreads to every cell in a monolayer. This effect also occurs when the protein is added exogenously. Internalization of SEQ ID NO: 2 protein is energy-independent and non-endocytic.

Because endocytosis is not involved in SEQ ID NO: 2 uptake, the system has additional advantages over other systems such as bacterial toxins or modified antibody. Those therapeutics are taken up by endocytosis resulting in possible retention of proteins for lengthy periods within endosomal vesicles excluded from the intracellular environment or degraded by lysosomes.

We link this bovine protein to desired therapeutic or reporter proteins for delivery to targeted tissues. This could be achieved by automated protein synthesizers. However, preferably we use DNA constructs to express the fusion protein. The linking of the transport/effector components is achieved through DNA engineering standard in gene therapy. Our system permits delivery of effector protein deep within tissue, whereas most other systems would only affect the surface or immediate delivery site.

Example 1

In Example 1 a known cancer suicide protein (ribotoxin restrictocin; SEQ ID NO: 3) was delivered to a solid tumor by linking the protein to the SEQ ID NO: 2 protein. The transport component carries the effector toxin along with it when the transport component spreads throughout the tumor. The tumor can then be more efficiently treated.

Example 2

We separately linked the SEQ ID NO: 2 protein to the SEQ ID NO: 4 protein to create a reporter system. This was accomplished using standard PCR and/or DNA subcloning techniques so as to have nucleotides 390 through 1161 of SEQ ID NO: 1 positioned 5' of the effector DNA (with the following intervening nucleotide sequences: acc ggt cgc, followed by an insertion of cac c), and a promotor 5' of the SEQ ID NO: 1 DNA.

PCR primers to SEQ ID NO: 1 were designed to include restriction enzyme sites so that PCR product could be inserted into the multiple cloning site of a standard expression plasmid and be in frame to the protein of interest. Additionally, the primer was designed to eliminate the stop codon at the 1163 nucleotide of SEQ ID NO: 1.

In this regard, beginning with the commercially available mammalian expression plasmid pEGFP-N1 (Clontech Laboratories, Inc; Palo Alto, Calif.), we formed plasmid pEGFP-U21137 as follows: U21137 was amplified from BHV-1 (bovine herpesvirus 1) DNA by the polymerase chain reaction (PCR) method utilizing primers designed to incorporate a BamHI 5' to the U21137 start codon and an Age I site at the 3' end which eliminated the U21137 stop codon. Both PCR product and mammalian expression vector pEGFP-N1 were digested with BamHI-Age I and purified. Digested U21137 PCR product was then subcloned into the BAMHI/Age I sites of pEGFP-N1 and the resultant construct, pEGFP-U21137, was tested for functionality by transfection, then fluorescent microscopy and Western blot analysis.

As shown in FIG. 1, the most significant features of this plasmid are a CMVp at bases 1–589, the U21137 insertion at bases 669–1455, the abutting GFP at bases 1456–2174, SV40pA at bases 2327–2361, f1 ori at bases 2424–2879, SV40p at bases 3053–3321, Kan/Neo at bases 3404–4198, HSV-TKpA at bases 4434–4452, and pUC ori at bases 4783–5426. While this construct shows the GFP 3' of the U21137, the order could be reversed. Further, the protein coding regions need not be immediately abutting.

Delivery Protocol

Fusion proteins themselves can be delivered to the desired tissue (e.g. in vitro or in vivo) by a wide variety of known techniques for delivering proteins, such as injection or oral administration.

However, we prefer to deliver the fusion protein endogenously via introduction of a DNA vector. This is preferably achieved in vitro by using the cationic lipid method. For example, by the cationic lipid method, cells were transfected using lipofectAMINE liposome reagent (Life Technologies, Inc.). Adherent cells were plated onto 6-well plates and grown until about 70% confluent and washed with 2 ml/well OPTI-MEM reduced-serum medium (Life Technologies, Inc.). After discarding the wash, 0.8 ml/well OPTI-MEM was added. Non-adherent cells in exponential grown phase were pelleted and washed with OPTI-MEM, pelleted and resuspended in OPTI-MEM at a concentration of $3 \times 10^6$ cells/ml.

Cells were plated at 0.8 ml/well. For each transfection (well), 1 $\mu$g of plasmid DNA in 100 $\mu$l OPTI-MEM was mixed with 6 $\mu$l LipofectAMINE in 100 $\mu$l OPTI-MEM. This mix (0.2 ml) was left to incubate at room temperature for at least 15 min before being added to the cells. After 3 h incubation at 37° C. in a humidified 5% $CO_2$ incubator, 1 ml/well of medium+20% FBS was added.

For in vivo introduction, we utilized two methods of delivering the system to the targeted tissues. When using the system for in vivo solid tumor destruction, we used microinjection of DNA. The nucleotide sequence was composed of SEQ ID NO: 2 intercellular transporter linked to the potent ribonucleotoxin, restrictocin (SEQ ID NO: 3). It was microinjected (1 cc syringe; 27 Ga needle) into a solid mouse mastocytoma. In this regard, purified DNA in physiologically balanced saline (PBS) solution (10 $\mu$g/ml) was injected (0.2 ml) directly into the tumor and the size of the tumor was monitored over several days. We noticed tumor diameter reduction compared to controls.

When using the system for in vivo DNA vaccination, we incorporated the biolistic process. Gold microparticles were coated with plasmid DNA and accelerated by a low-pressure helium hand held device to bombard tissue. Blood samples were taken periodically and assayed by ELISA for effective antibody response.

Comparative Experiments

We also conducted comparative experiments to determine the relative efficacy of fusion proteins constructed in accordance with the present invention as compared with fusion proteins linking human VP22 to an effector protein. Osteosarcoma cells were transiently transfected with constructs consisting of green fluorescent protein effector linked to either human VP22 or the SEQ ID NO: 2 protein. Controls consisted of the fluorescent protein by itself.

In one set of experiments, transfected cell lysates were separated on 10% SDS-PAGE and proteins transferred to nitrocellulose. Specific expression was assayed using an antibody to the fluorescent protein to permit chemiluminescent detection. In another set of experiments, monolayers of rat mammary tumor cells, and cow and monkey kidney cells were transfected with reporter fusion product. SEQ ID NO:

2 fusion protein spread through a monolayer of cells significantly more intensely than VP22 fusion constructs.

While specific constructs have been shown, it should be appreciated that the gap between the end of the bovine gene or protein and the beginning of the effector protein may be of varying lengths. Moreover, proteins which are at least 80% (more preferably at least 90%) as long as the SEQ ID NO: 2 protein, and at least 80% identical (more preferably at least 90% identical) to the SEQ ID NO: 2 protein (insofar as their region of greatest homology over a region at least as large as 80% of the SEQ ID NO: 2 protein length, using the BLAST analysis method using default settings), and which also facilitate trafficking function, are intended to be within the scope of the term "SEQ ID NO: 2 bovine herpesvirus protein".

INDUSTRIAL APPLICABILITY

The invention provides systems for delivering therapeutic drugs and reporters to desired cellular locations.

---

We claim:

1. A peptide comprising SEQ ID NO: 2 bovine herpesvirus protein linked to a non-bovine reporter protein.

2. The peptide of claim 1 wherein the non-bovine protein is a fluorescent protein.

3. A nucleotide sequence coding for SEQ ID NO: 2 bovine herpesvirus protein linked to a non-bovine reporter protein.

4. A nucleotide vector comprising a vector backbone and a nucleotide sequence coding for SEQ ID NO: 2 bovine herpesvirus protein linked to a non-bovine reporter protein.

* * * * *

SEQUENCE LISTING

<160> NUMBER OF SEQ ID NOS: 4

<210> SEQ ID NO 1
<211> LENGTH: 1499
<212> TYPE: DNA
<213> ORGANISM: Bovine herpesvirus 1
<220> FEATURE:
<221> NAME/KEY: CDS
<222> LOCATION: (390)..(1166)

<400> SEQUENCE: 1

```
cggttgtggc cgccgcgctg tttgccatcg tgcgcggccg cgaccccctg ctagacgcga      60
tgcggcgcga gggggcaatg gacttttgga gcgcaggctg ctacgcgcgc ggggtgccgc     120
tctcggagcc accgcaggcc ctggttgttt tttacgtggc cctgaccgcg gtaatggtcg     180
ccgtggccct gtacgcgtac gggctttgct ttaggctcat gggcgccagc gggcccaata     240
aaaaggagtc gcgggggcgg ggctgattga ccgcaacgct gcggagtaac ttgtatataa     300
agctcgcggt cccggcgacc gctgcctttt tcgcactcgg cccgacccgc tttgagctgc     360
acgcccgccg gcccgccgac tcgcttgcc atg gcc cgg ttc cac agg ccc tcc      413
                                  Met Ala Arg Phe His Arg Pro Ser
                                   1               5 gaa gac gag gac gat tac gag tac agc gac ctt tgg gtg cga gaa aac      461
Glu Asp Glu Asp Asp Tyr Glu Tyr Ser Asp Leu Trp Val Arg Glu Asn
         10                  15                  20 agc ctc tat gac tac gag tcc ggc tcg gat gac cac gta tac gaa gag      509
Ser Leu Tyr Asp Tyr Glu Ser Gly Ser Asp Asp His Val Tyr Glu Glu
 25                  30                  35                  40 ctg cgc gcc gcg acg agc gga ccc gag ccg agc ggg cgg cgc gct agc      557
Leu Arg Ala Ala Thr Ser Gly Pro Glu Pro Ser Gly Arg Arg Ala Ser
             45                  50                  55 gtc cgt gcg tgc gcc agc gct gca gcc gtc cag ccc gcc gcc cgc ggc      605
Val Arg Ala Cys Ala Ser Ala Ala Ala Val Gln Pro Ala Ala Arg Gly
         60                  65                  70 cgc gat cga gcc gca gcc gcg ggg acg acc gta gct gcg ccc gcc gcc      653
Arg Asp Arg Ala Ala Ala Ala Gly Thr Thr Val Ala Ala Pro Ala Ala
     75                  80                  85 gcg ccg gcc cgc cgc tcg agc agc cgg gcg tcc tcg cgc ccg ccg cga      701
Ala Pro Ala Arg Arg Ser Ser Ser Arg Ala Ser Ser Arg Pro Pro Arg
 90                  95                 100 gct gcc gcc gac ccg ccc gtc ctc cgg cca gcc acg cgc ggg tcc tcc      749
Ala Ala Ala Asp Pro Pro Val Leu Arg Pro Ala Thr Arg Gly Ser Ser
105                 110                 115                 120 ggc ggc gcc ggg gca gtc gcc gtc ggt cca cct cga cct cgc gcg ccc      797
Gly Gly Ala Gly Ala Val Ala Val Gly Pro Pro Arg Pro Arg Ala Pro
             125                 130                 135 ccc ggt gct aat gct gtt gcg tct ggc cgg ccg ctg gcg ttc agc gcg      845
Pro Gly Ala Asn Ala Val Ala Ser Gly Arg Pro Leu Ala Phe Ser Ala
```

-continued

| | | |
|---|---|---|
| gct ccg aaa acg ccc aag gcg ccc tgg tgt gga ccg acg cac gcc tac<br>Ala Pro Lys Thr Pro Lys Ala Pro Trp Cys Gly Pro Thr His Ala Tyr<br>    155                 160                 165 | 893 |
| aac cga acg atc ttt tgc gag gcc gtc gcg ctc gtg gcc gcc gag tac<br>Asn Arg Thr Ile Phe Cys Glu Ala Val Ala Leu Val Ala Ala Glu Tyr<br>    170                 175                 180 | 941 |
| gcc cgg cag gcg gct gcc agc gtc tgg gac tcg gac ccc cca aag agc<br>Ala Arg Gln Ala Ala Ala Ser Val Trp Asp Ser Asp Pro Pro Lys Ser<br>185                 190                 195                 200 | 989 |
| aac gag cga ttg gat cgc atg ttg aag tcg gcg gca att cgc atc ctc<br>Asn Glu Arg Leu Asp Arg Met Leu Lys Ser Ala Ala Ile Arg Ile Leu<br>                205                 210                 215 | 1037 |
| gtg tgc gag ggc tcc ggg ctt ctc gcc gcc gcg aac gac atc ttg gcc<br>Val Cys Glu Gly Ser Gly Leu Leu Ala Ala Ala Asn Asp Ile Leu Ala<br>    220                 225                 230 | 1085 |
| gcg cgg gcc cag cgc ccc gcc gcg cgc ggg agc aca agc ggc ggg gaa<br>Ala Arg Ala Gln Arg Pro Ala Ala Arg Gly Ser Thr Ser Gly Gly Glu<br>    235                 240                 245 | 1133 |
| agc cgc ctt cgc ggc gag cgg gcc cgg ccg tag cgcgagcggg agggctttt<br>Ser Arg Leu Arg Gly Glu Arg Ala Arg Pro<br>    250                 255 | 1186 |
| cgacgcgcgc ggcttaagca gcgcgctgct gtgctagtat gaaaataaac gcttgttaat | 1246 |
| taaacacacc aagccgagtt gcgttgtctt tgggatgagc gggcgcataa aaaccgcggg | 1306 |
| ccgcgcgctc gccagtcagt gcggcggtgc tgcggcggca accatggacc cgtacgacgc | 1366 |
| cattgaagcg ttcgatgact ccctgctcgg gtcgccgctc gcggcggggc cgctttatga | 1426 |
| cggcccgtcc cccgcgcggt tcgcgctgcc gccccgcgc ccggctcccc tggccgcgtt | 1486 |
| gctggagcga atg | 1499 |

<210> SEQ ID NO 2
<211> LENGTH: 258
<212> TYPE: PRT
<213> ORGANISM: Bovine herpesvirus 1

<400> SEQUENCE: 2

Met Ala Arg Phe His Arg Pro Ser Glu Asp Glu Asp Tyr Glu Tyr
1               5                   10                  15

Ser Asp Leu Trp Val Arg Glu Asn Ser Leu Tyr Asp Tyr Glu Ser Gly
            20                  25                  30

Ser Asp Asp His Val Tyr Glu Glu Leu Arg Ala Ala Thr Ser Gly Pro
        35                  40                  45

Glu Pro Ser Gly Arg Arg Ala Ser Val Arg Ala Cys Ala Ser Ala Ala
    50                  55                  60

Ala Val Gln Pro Ala Ala Arg Gly Arg Asp Arg Ala Ala Ala Gly
65                  70                  75                  80

Thr Thr Val Ala Ala Pro Ala Ala Pro Ala Arg Arg Ser Ser
                85                  90                  95

Arg Ala Ser Ser Arg Pro Pro Arg Ala Ala Asp Pro Pro Val Leu
                100                 105                 110

Arg Pro Ala Thr Arg Gly Ser Ser Gly Gly Ala Gly Ala Val Ala Val
            115                 120                 125

Gly Pro Pro Arg Pro Arg Ala Pro Gly Ala Asn Ala Val Ala Ser
        130                 135                 140

Gly Arg Pro Leu Ala Phe Ser Ala Ala Pro Lys Thr Pro Lys Ala Pro
145                 150                 155                 160

```
Trp Cys Gly Pro Thr His Ala Tyr Asn Arg Thr Ile Phe Cys Glu Ala
                165                 170                 175

Val Ala Leu Val Ala Ala Glu Tyr Ala Arg Gln Ala Ala Ala Ser Val
            180                 185                 190

Trp Asp Ser Asp Pro Pro Lys Ser Asn Glu Arg Leu Asp Arg Met Leu
        195                 200                 205

Lys Ser Ala Ala Ile Arg Ile Leu Val Cys Glu Gly Ser Gly Leu Leu
    210                 215                 220

Ala Ala Ala Asn Asp Ile Leu Ala Leu Arg Ala Gln Arg Pro Ala Ala
225                 230                 235                 240

Arg Gly Ser Thr Ser Gly Gly Glu Ser Arg Leu Arg Gly Glu Arg Ala
            245                 250                 255

Arg Pro

<210> SEQ ID NO 3
<211> LENGTH: 176
<212> TYPE: PRT
<213> ORGANISM: Aspergillus restrictus

<400> SEQUENCE: 3

Met Val Ala Ile Lys Asn Leu Phe Leu Leu Ala Ala Thr Ala Val Ser
1               5                   10                  15

Val Leu Ala Ala Pro Ser Pro Leu Asp Ala Arg Ala Thr Trp Thr Cys
            20                  25                  30

Ile Asn Gln Gln Leu Asn Pro Lys Thr Asn Lys Trp Glu Asp Lys Arg
        35                  40                  45

Leu Leu Tyr Ser Gln Ala Lys Ala Glu Ser Asn Ser His His Ala Pro
    50                  55                  60

Leu Ser Asp Gly Lys Thr Gly Ser Ser Tyr Pro His Trp Phe Thr Asn
65                  70                  75                  80

Gly Tyr Asp Gly Asn Gly Lys Leu Ile Lys Gly Arg Thr Pro Ile Lys
                85                  90                  95

Phe Gly Lys Ala Asp Cys Asp Arg Pro Pro Lys His Ser Gln Asn Gly
            100                 105                 110

Met Gly Lys Asp Asp His Tyr Leu Leu Glu Phe Pro Thr Phe Pro Asp
        115                 120                 125

Gly His Asp Tyr Lys Phe Asp Ser Lys Lys Pro Lys Glu Asp Pro Gly
    130                 135                 140

Pro Ala Arg Val Ile Tyr Thr Tyr Pro Asn Lys Val Phe Cys Gly Ile
145                 150                 155                 160

Val Ala His Gln Arg Gly Asn Gln Gly Asp Leu Arg Leu Cys Ser His
                165                 170                 175

<210> SEQ ID NO 4
<211> LENGTH: 238
<212> TYPE: PRT
<213> ORGANISM: Aequorea victoria

<400> SEQUENCE: 4

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45
```

-continued

```
Thr Thr Gly Lys Leu Pro Val Pro Trp Pro Thr Leu Val Thr Thr Phe
     50                  55                  60

Ser Tyr Gly Val Gln Cys Phe Ser Arg Tyr Pro Asp His Met Lys Gln
 65                 70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Ser Arg Ala Glu Val
            100                 105                 110
Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
    210                 215                 220
Thr Ala Ala Gly Ile Thr His Gly Met Asp Glu Leu Tyr Lys
225                 230                 235
```